United States Patent
Kawabata et al.

(10) Patent No.: US 12,138,021 B2
(45) Date of Patent: Nov. 12, 2024

(54) BIOMETRIC DATA MEASUREMENT SYSTEM AND BIOMETRIC DATA MEASUREMENT METHOD

(71) Applicants: OMRON HEALTHCARE Co., Ltd., Kyoto (JP); OMRON Corporation, Kyoto (JP)

(72) Inventors: Yasuhiro Kawabata, Kyoto (JP); Kenji Fujii, Kyoto (JP); Naomi Matsumura, Kyoto (JP); Reiji Fujita, Kyoto (JP); Akito Ito, Kyoto (JP)

(73) Assignees: OMRON HEALTHCARE CO., LTD., Kyoto (JP); OMRON CORPORATION, Kyoto (JP)

( * ) Notice: Subject to any disclaimer, the term of this patent is extended or adjusted under 35 U.S.C. 154(b) by 863 days.

(21) Appl. No.: 17/146,966

(22) Filed: Jan. 12, 2021

(65) Prior Publication Data
US 2021/0127994 A1  May 6, 2021

Related U.S. Application Data

(63) Continuation of application No. PCT/JP2019/026085, filed on Jul. 1, 2019.

(30) Foreign Application Priority Data

Jul. 20, 2018 (JP) ................. 2018-137109

(51) Int. Cl.
*A61B 5/021* (2006.01)
*G06F 3/01* (2006.01)
(Continued)

(52) U.S. Cl.
CPC .......... *A61B 5/02125* (2013.01); *G06F 3/015* (2013.01); *G06V 40/50* (2022.01); *G06F 2218/16* (2023.01); *G06V 40/15* (2022.01)

(58) Field of Classification Search
CPC .......... A61B 5/02; A61B 5/0205; A61B 5/021; A61B 5/02125; A61B 5/02108;
(Continued)

(56) References Cited

U.S. PATENT DOCUMENTS

| | | | |
|---|---|---|---|
| 2007/0042728 A1* | 2/2007 | Pan ..................... | H04B 1/30 455/127.1 |
| 2010/0159835 A1* | 6/2010 | Aoki .................... | A61B 5/0002 455/41.3 |
| 2011/0237965 A1* | 9/2011 | Hayashi ............. | A61B 5/02416 600/500 |
| 2012/0009875 A1 | 1/2012 | Miettinen et al. | |
| 2014/0155767 A1* | 6/2014 | Fukuda .............. | A61B 5/02125 600/485 |

(Continued)

FOREIGN PATENT DOCUMENTS

| | | |
|---|---|---|
| CN | 103845046 A | 6/2014 |
| CN | 104582564 A | 4/2015 |

(Continued)

OTHER PUBLICATIONS

International Preliminary Report on Patentability and Written Opinion of The International Searching Authority issued Jan. 26, 2021 in International (PCT) Application No. PCT/JP2019/026085.

*Primary Examiner* — Daniel L Cerioni
*Assistant Examiner* — Andrew E Hoffpauir
(74) *Attorney, Agent, or Firm* — Wenderoth, Lind & Ponack, L.L.P.

(57) ABSTRACT

A biometric data measurement system and method, including a transmitting device including a measurement unit configured to measure a first biometric data, a setting unit configured to set a first reference time corresponding to an occurrence time of a first feature value of the first biometric data, and a transmission unit configured to transmit a signal at a time when a predetermined first time period has elapsed (Continued)

since the first reference time, and a receiving device including a measurement unit configured to measure a second biometric data, a setting unit configured to set a second reference time corresponding to an occurrence time of a second feature value of the second biometric data, and a reception unit configured to maintain an awaiting state for the signal during a third time period from a time when a second time period has elapsed since the second reference time.

6 Claims, 8 Drawing Sheets

(51) Int. Cl.
    *G06V 40/10*     (2022.01)
    *G06V 40/50*     (2022.01)
(58) Field of Classification Search
    CPC ............. A61B 5/0245; A61B 5/02416; A61B 5/0295; A61B 5/0006; A61B 5/349; A61B 5/352; A61B 5/7285; A61B 2560/0238
    See application file for complete search history.

(56) References Cited

U.S. PATENT DOCUMENTS

| | | | |
|---|---|---|---|
| 2015/0230706 A1* | 8/2015 | Nakagawa | A61B 5/335 340/870.07 |
| 2015/0303990 A1* | 10/2015 | Chen | H04B 17/382 375/132 |
| 2017/0119318 A1* | 5/2017 | Shay | A61B 5/7225 |
| 2017/0150891 A1 | 6/2017 | Tsuchimoto et al. | |
| 2017/0212739 A1* | 7/2017 | Catiller | G06F 15/7889 |
| 2018/0214039 A1* | 8/2018 | Lee | A61B 5/352 |
| 2018/0310852 A1* | 11/2018 | Kendricks | A61B 5/28 |

FOREIGN PATENT DOCUMENTS

| | | |
|---|---|---|
| EP | 2404548 A2 | 1/2012 |
| JP | 2014-108141 A | 6/2012 |
| JP | 6202510 B1 | 9/2017 |
| WO | 2014/033942 A1 | 3/2014 |
| WO | 2016/024476 A1 | 2/2016 |
| WO | 2018/142821 A1 | 8/2018 |

\* cited by examiner

[FIG. 4]
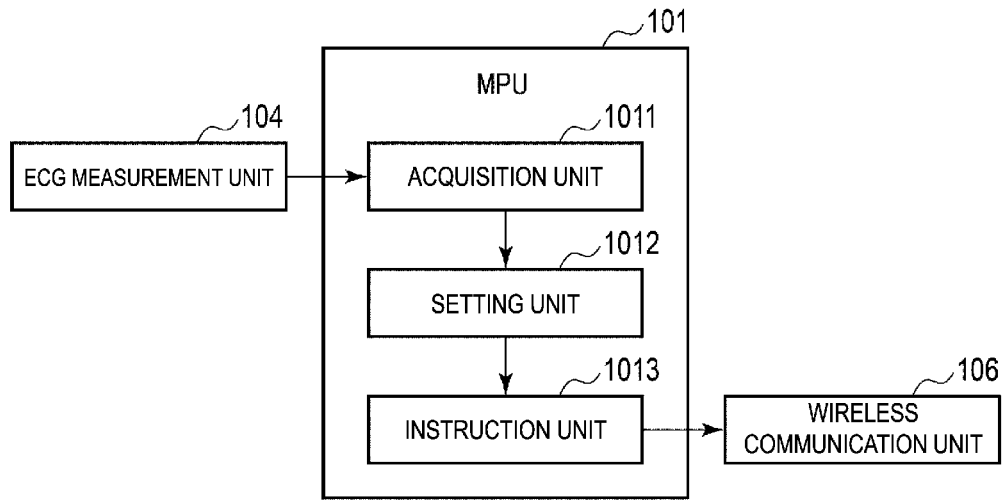
[FIG. 5]
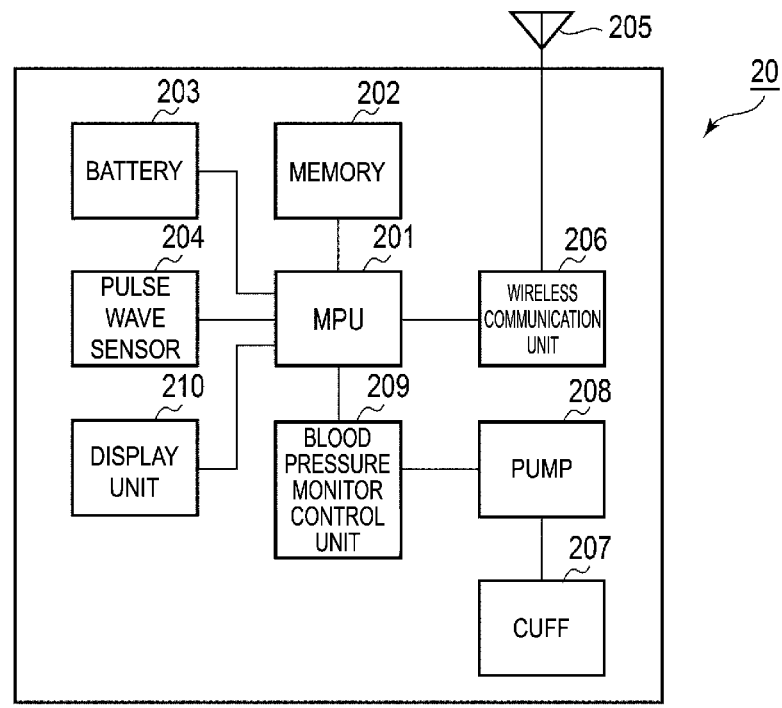

[FIG. 6]
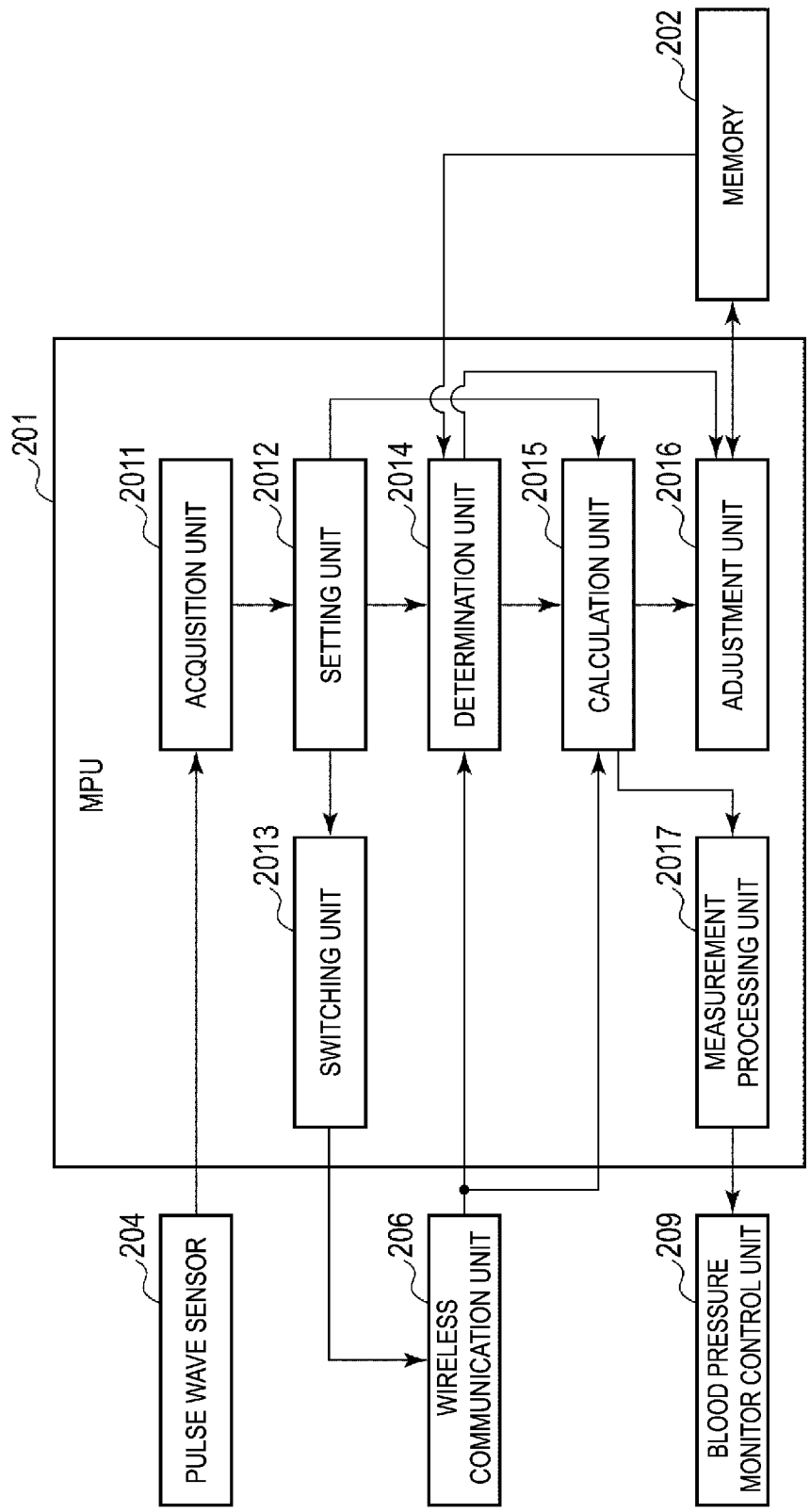

[FIG. 7]
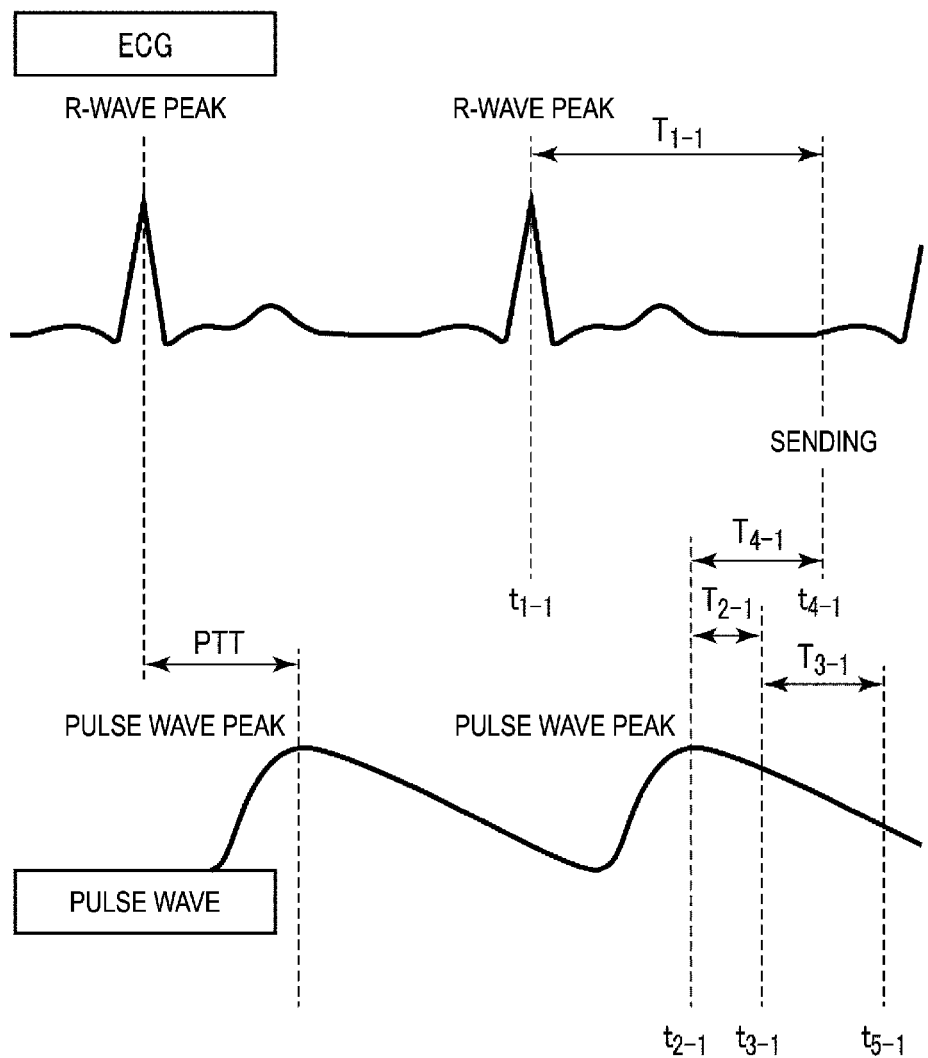

[FIG. 8]
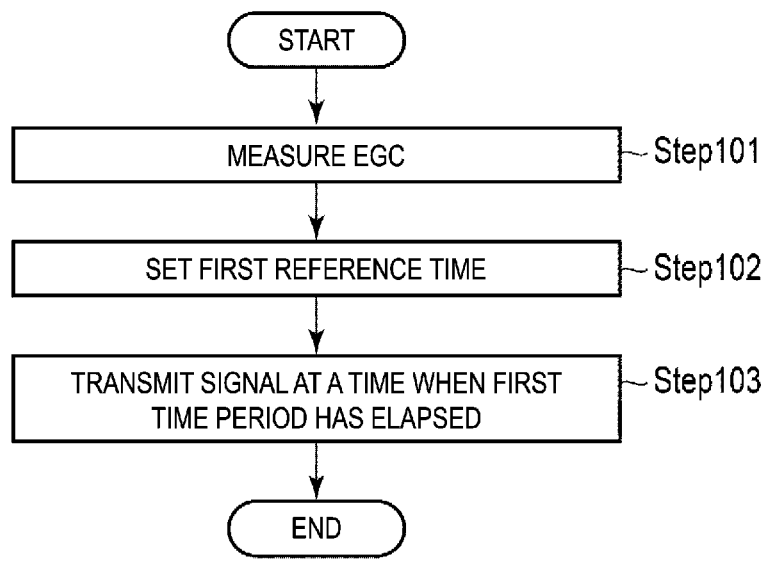

[FIG. 9]
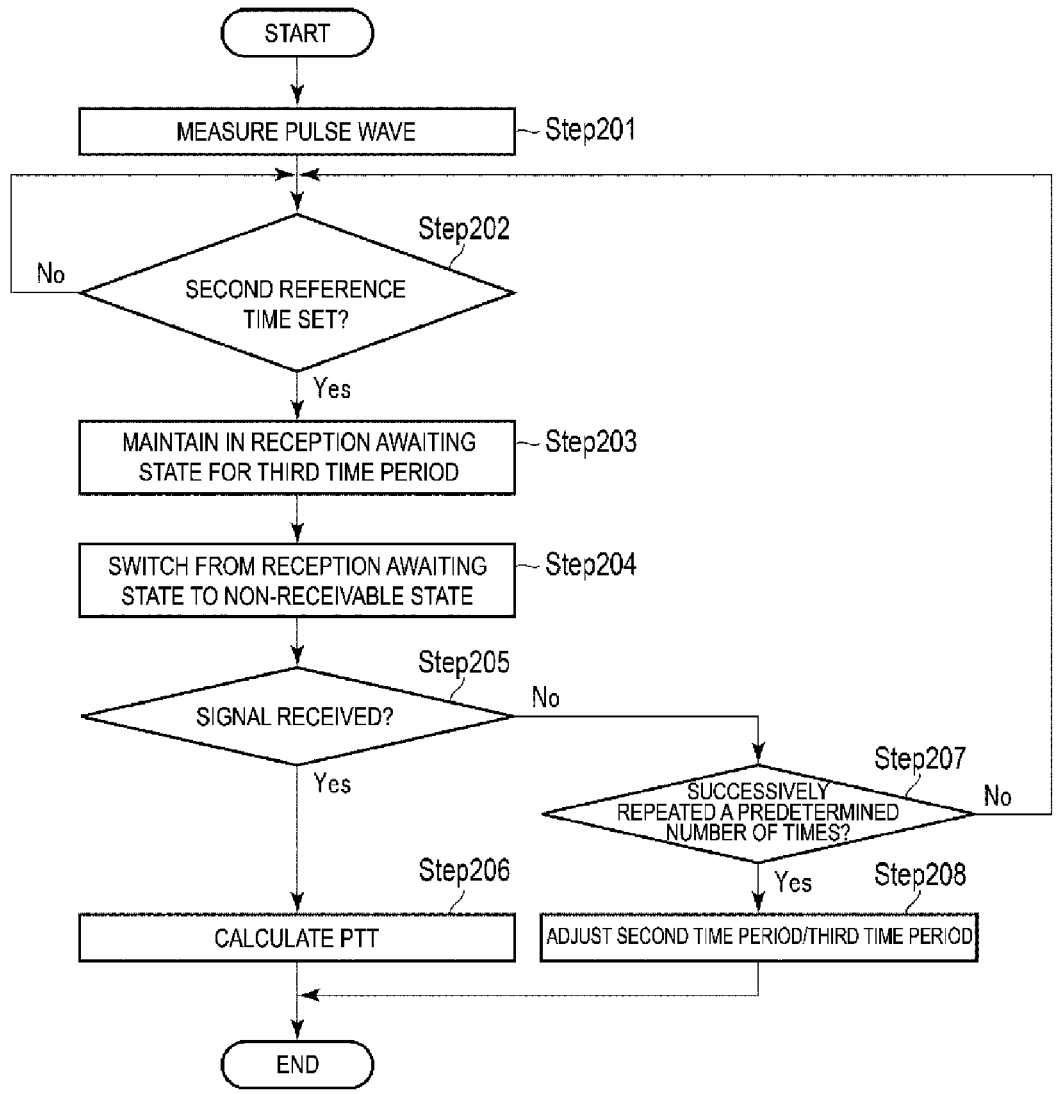

[FIG. 10]
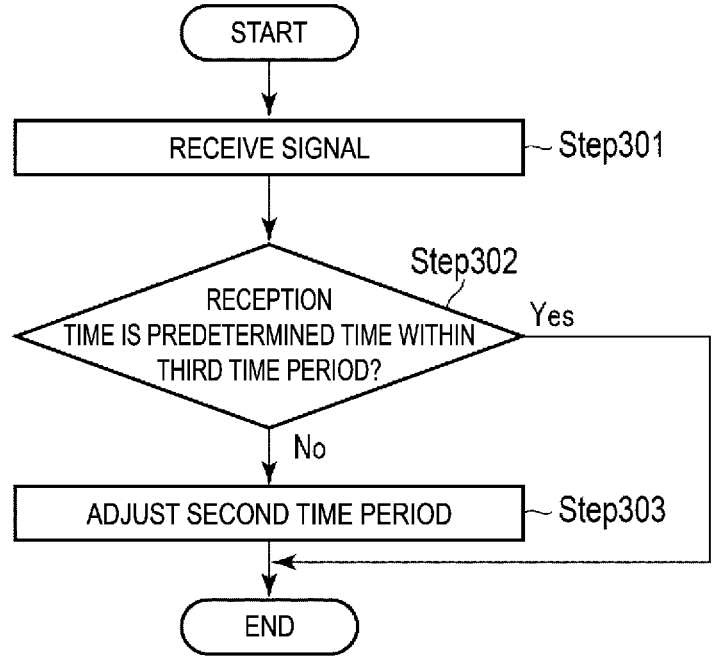
[FIG. 11]
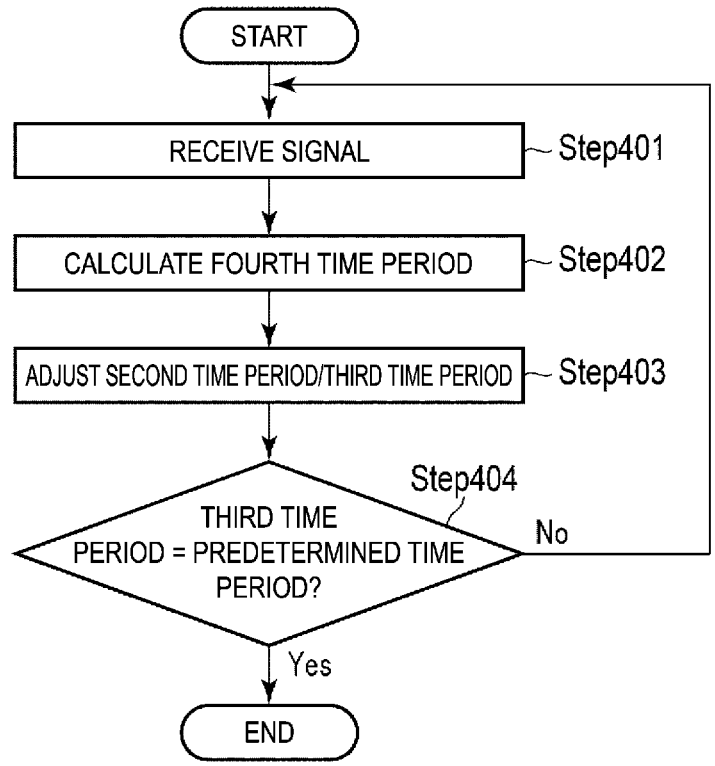

BIOMETRIC DATA MEASUREMENT SYSTEM AND BIOMETRIC DATA MEASUREMENT METHOD

CROSS-REFERENCE TO RELATED APPLICATIONS

This application is the U.S. national stage application filed pursuant to 35 U.S.C. 365(c) and 120 as a continuation of International Patent Application No. PCT/JP2019/026085, filed Jul. 1, 2019, which application claims priority from Japanese Patent Application No. 2018-137109, filed Jul. 20, 2018, which applications are incorporated herein by reference in their entireties.

TECHNICAL FIELD

The invention relates to a biometric data measurement system and a biometric data measurement method.

BACKGROUND ART

The correlation between pulse transit time (PTT) and blood pressure is known. This correlation allows blood pressure to be estimated on the basis of the PTT.

Also, technologies for measuring PTT on the basis of an electrocardiogram (ECG) and pulse waves are known. For example, a system for estimating blood pressure on the basis of PTT may include a device for measuring ECG and a device for measuring pulse waves.

When the device for measuring ECG and the device for measuring pulse waves have a wired connection, attaching the two devices to a human body may be a laborious task. In Patent Document 1, a biological information sensor is described including two devices wirelessly connected to allow for the two devices to be easily attached to a human body.

CITATION LIST

Patent Literature

Patent Document 1: WO 2016/024476

SUMMARY OF INVENTION

Technical Problem

However, in the biological information sensor described in Patent Document 1, the pulse wave waveform data measured by a pulse wave sensor device is transmitted wirelessly as is to a signal processing unit. In this case, both devices need to constantly ensure a communicative state. Thus, the power consumption of a transmitting device and a receiving device is increased.

The present invention is directed at the circumstances described above and has an object to provide a biometric data measurement system and a biometric data measurement method that allow easy attachment to a human body and have low power consumption.

Solution to Problem

A first aspect of the present disclosure is a biometric data measurement system that includes a transmitting device including a measurement unit configured to measure a first biometric data, a setting unit configured to set a first reference time corresponding to an occurrence time of a first feature value of the first biometric data, and a transmission unit configured to transmit a signal at a time when a predetermined first time period has elapsed since the first reference time, and a receiving device including a measurement unit configured to measure a second biometric data, a setting unit configured to set a second reference time corresponding to an occurrence time of a second feature value of the second biometric data, and a reception unit configured to maintain an awaiting state for the signal during a third time period from a time when a second time period has elapsed since the second reference time.

According to the first aspect, the timing of the signal transmission by the transmitting device is determined on the basis of the first reference time, which corresponds to the occurrence time of the first feature value of the first biometric data. The transmitting device is at least only required to transmit a signal between the first reference time and the time when the first time period has elapsed since the first reference time. The transmitting device is not necessarily required to constantly ensure a communicative state. As such, the transmitting device can reduce the power consumption required for communication.

Furthermore, the third time period for awaiting a signal is determined on the basis of the second reference time corresponding to the occurrence time of the second feature value of the second biometric data. The receiving device can successfully communicate with the transmitting device as long as the receiving device is awaiting the signal in the third time period. The receiving device is not necessarily required to constantly ensure a communicative state. As such, the receiving device can reduce the power consumption required for communication.

Accordingly, the biometric data measurement system can not only be easily attached to the human body, but also can reduce power consumption.

In a second aspect of the present disclosure according to the first aspect, the receiving device further includes a calculation unit configured to calculate a fourth time period from the second reference time to a reception time of the signal and calculate a PTT on the basis of a time difference between the first time period and the fourth time period.

Because the timing of the transmitting device transmitting a signal is based on the first reference time, the receiving device can calculate the PTT by simply calculating the time difference between the first time period and the fourth time period.

By the receiving device being able to calculate the PTT without constantly communicating with the transmitting device, the power consumption required for communication can be reduced.

In a third aspect of the present disclosure according to the first aspect, the receiving device further includes an adjustment unit configured to adjust at least one of a length of the second time period and a length of the third time period on the basis of non-reception of the signal successively occurring a predetermined number of times within the third time period.

Depending on a change in the PTT due to fluctuations in the blood pressure, the period from the second reference time to a time when a signal arrives at the receiving device changes. The receiving device can stop continuing the state in which a signal reaching the receiving device is not received.

In a fourth aspect of the present disclosure according to the first aspect, the receiving device further includes an adjustment unit configured to adjust a length of the second time period causing a reception time of the signal being closer to a predetermined time within the third time period when the reception time of the signal is not the predetermined time within the third time period.

Depending on a change in the PTT due to fluctuations in the blood pressure, the period from the second reference time to a time when a signal arrives at the receiving device may shorten or lengthen. By adjusting the length of the second time period, the receiving device can reduce the possibility of a signal not being received even when the time period from the second reference time to a time when the signal arrives at the receiving device changes depending on a change in the PTT.

In a fifth aspect of the present disclosure according to the first aspect, the receiving device further includes a calculation unit configured to calculate a fourth time period from the second reference time to a reception time of the signal, and an adjustment unit configured to adjust at least one of a length of the second time period and a length of the third time period for each calculation of the fourth time period.

This allows the receiving device to set an optimal second time period and third time period for each user. Furthermore, because the third time period can be shortened to the minimum necessary length, the receiving device can reduce the power consumption.

In a sixth aspect of the present disclosure according to the first aspect, the first biometric data is an ECG, and the second biometric data is a pulse wave.

The amount of power is obtained by the product of power and time. The current value is larger for the transmitting device than the receiving device. On the other hand, the third time period during which the receiving device awaits the signal is longer than the time period in which the transmitting device transmits the signal. As such, the amount of power consumed is larger for the receiving device than the transmitting device. Here, the quality of the pulse wave waveform may be worse than the quality of the ECG waveform. Unless the second feature value of the pulse wave is detected, the receiving device does not switch from the non-receivable state to the reception awaiting state. As such, the receiving device can reduce power consumption because it does not undesirably switch from the non-receivable state to the reception awaiting state.

A seventh aspect of the present disclosure is a biometric data measurement method includes measuring a first biometric data by a transmitting device, setting a first reference time corresponding to an occurrence time of a first feature value of the first biometric data by the transmitting device, transmitting a signal at a time when a predetermined first time period has elapsed since the first reference time by the transmitting device, measuring a second biometric data by a receiving device, setting a second reference time corresponding to an occurrence time of a second feature value of the second biometric data by the receiving device, and maintaining an awaiting state for the signal during a third time period from a time when a second time period has elapsed since the second reference time by the receiving device.

According to a seventh aspect, the biometric data measurement method can obtain the same effects as those of the first aspect described above.

Advantageous Effects of Invention

The present invention provides a biometric data measurement system and a biometric data measurement method that allow easy attachment to a human body and have low consumption of power required for communication.

BRIEF DESCRIPTION OF DRAWINGS

FIG. 4 is a block diagram illustrating an example of the software configuration of the ECG measurement device according to the present embodiment.

FIG. 5 is a block diagram illustrating an example of the hardware configuration of a pulse wave measurement device according to the present embodiment.

FIG. 6 is a block diagram illustrating an example of the software configuration of a pulse wave measurement device according to the present embodiment.

FIG. 7 is a diagram illustrating an example of the timing of the transmission and the reception of a signal in the biometric data measurement system according to the present embodiment.

FIG. 8 is a flowchart illustrating an example of signal transmission processing by the ECG measurement device according to the present embodiment.

FIG. 9 is a flowchart illustrating an example of signal reception processing by the pulse wave measurement device according to the present embodiment.

FIG. 10 is a flow chart illustrating an example of adjustment processing by the pulse wave measurement device according to the present embodiment.

FIG. 11 is a flow chart illustrating another example of adjustment processing by the pulse wave measurement device according to the present embodiment.

DESCRIPTION OF EMBODIMENTS

An embodiment according to the present invention (hereinafter, also referred to as "the present embodiment") will be described below with reference to the drawings. However, the present embodiment described below is merely an example in all respects. Note that elements that are the same as or similar to the elements described hereinafter are given the same or similar reference signs, and duplicate descriptions will be omitted. Note that although data appearing in the present embodiment will be described using natural language, the data is more specifically designated by pseudo-language, commands, parameters, machine language, and the like.

1. SUMMARY

The present embodiment relates to a biometric data measurement system including a transmitting device configured to measure biometric data and a receiving device that are wirelessly connected. The receiving device calculates the PTT on the basis of reception of a signal transmitted from the transmitting device at a predetermined timing. The receiving device estimates blood pressure on the basis of PTT. The timing of the signal transmission from the transmitting device and the signal reception by the receiving device is set to match or substantially match the cycle of the biometric data.

Figure 1:
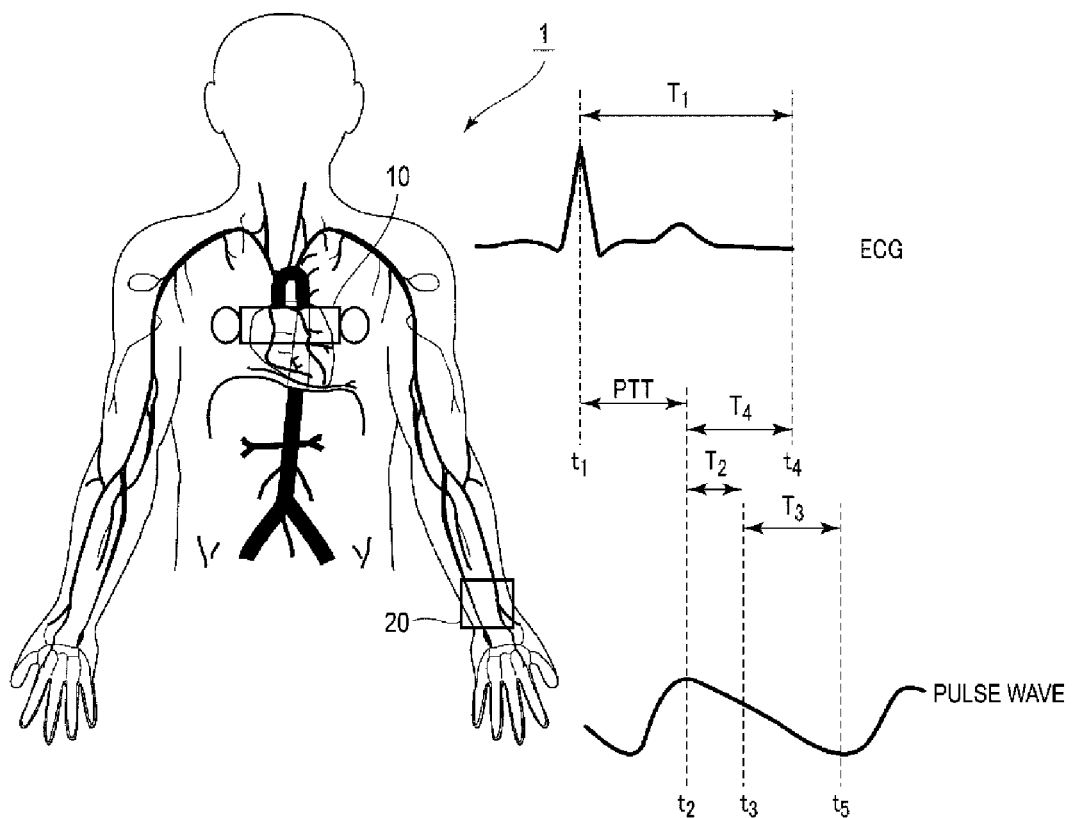
FIG. 1 is a diagram schematically illustrating an overview of a biometric data measurement system according to the present embodiment.

FIG. 1 is a diagram schematically illustrating an overview of a biometric data measurement system 1.

The biometric data measurement system 1 includes an ECG measurement device 10 and a pulse wave measurement device 20. The biometric data measurement system 1 is a system that calculates PTT without sharing, between the ECG measurement device 10 and the pulse wave measurement device 20, the information indicative of the occurrence time of the peak in the ECG, occurrence time of the peak in a pulse wave, and the like.

The ECG measurement device 10 is a device for measuring ECG. The ECG measurement device 10 is disposed with two electrodes on either side of the heart of a human body. ECG measurement device 10 detects peaks in the ECG. The ECG measurement device 10 detects the occurrence time of an ECG peak on the basis of the detection of an ECG peak. The ECG measurement device 10 sets a first reference time $t_1$ corresponding to the occurrence time of the ECG peak. The ECG measurement device 10 transmits a signal to the pulse wave measurement device 20 at a time $t_4$ when a predetermined first time period $T_1$ has elapsed since the first reference time $t_1$.

A pulse wave measurement device 20 is a device for measuring pulse waves. The pulse wave measurement device 20 is placed at a predetermined position on the human body. The pulse wave measurement device 20 detects peaks in the pulse waves. The pulse wave measurement device 20 detects the occurrence time of a pulse wave peak on the basis of the detection of a pulse wave peak. The pulse wave measurement device 20 sets a second reference time $t_2$ corresponding to the occurrence time of the pulse wave peak. The pulse wave measurement device 20 maintains a state of awaiting a signal during a third time period $T_3$ from a time $t_3$ when a second time period $T_2$ has elapsed since the second reference time $t_2$. A fourth time period $T_4$ is a time period from the second reference time $t_2$ to the time $t_4$, which is the reception time of the signal. The difference in time between the first time period $T_1$ and the fourth time period $T_4$ corresponds to the interval between the first reference time $t_1$ and the second reference time $t_2$. The pulse wave measurement device 20 calculates the PTT on the basis of the time difference between the first time period $T_1$ and the fourth time period $T_4$. In this way, the pulse wave measurement device 20 can calculate the PTT on the basis of the predetermined first time period $T_1$ and the fourth time period $T_4$ measured by the pulse wave measurement device 20 without sharing information indicative of the first reference time $t_1$ between the ECG measurement device 10 and the pulse wave measurement device 20. The pulse wave measurement device 20 estimates blood pressure on the basis of the PTT.

In this way, the timing of the signal transmission by the ECG measurement device 10 is determined on the basis of the first reference time $t_1$, which corresponds to the occurrence time of the ECG peak. The ECG measurement device 10 is at least only required to transmit a signal between the first reference time $t_1$ and the time $t_4$ when the first time period $T_1$ has elapsed since the first reference time $t_1$. The ECG measurement device 10 is not necessarily required to constantly ensure a communicative state. As such, the ECG measurement device 10 can reduce the power consumption required for communication.

Furthermore, the third time period $T_3$ for awaiting a signal is determined on the basis of the second reference time $t_2$ corresponding to the occurrence time of the pulse wave peak. The pulse wave measurement device 20 can successfully communicate with the ECG measurement device 10 as long as the pulse wave measurement device 20 is awaiting the signal in the third time period $T_3$. The pulse wave measurement device 20 is not necessarily required to constantly ensure a communicative state. As such, the pulse wave measurement device 20 can reduce the power consumption required for communication.

Accordingly, the biometric data measurement system 1 can not only be easily attached to the human body, but also can reduce power consumption.

2 CONFIGURATION EXAMPLE

Biometric Data Measurement System

Figure 2:
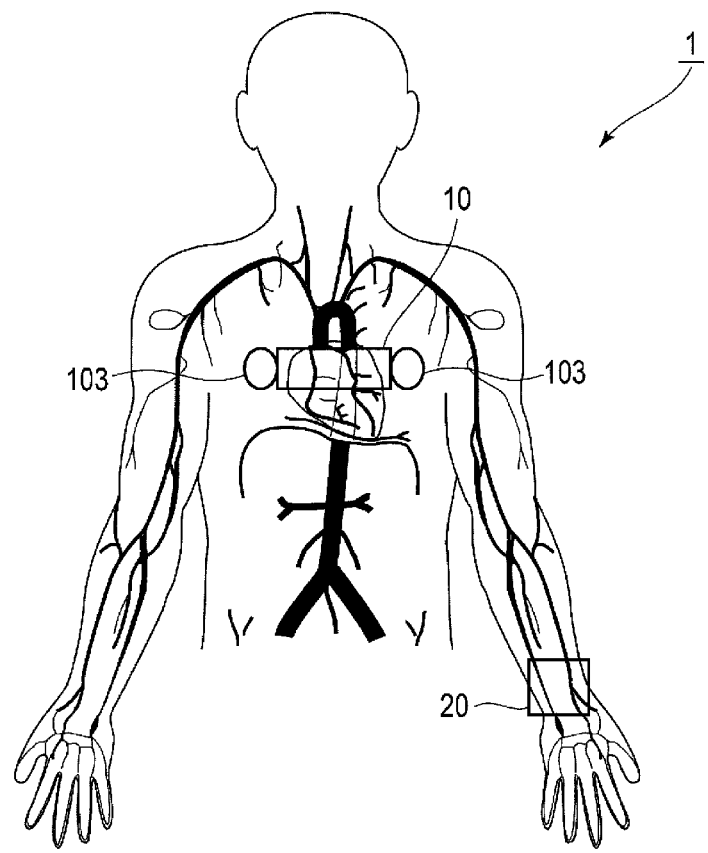
FIG. 2 is a diagram illustrating an example of the configuration of the biometric data measurement system according to the present embodiment.

FIG. 2 is a diagram illustrating the configuration of the biometric data measurement system 1.

The biometric data measurement system 1 includes an ECG measurement device 10 and a pulse wave measurement device 20. The ECG measurement device 10 and the pulse wave measurement device 20 communicate wirelessly. Herein, an example in which the ECG measurement device 10 transmits a signal to the pulse wave measurement device 20 will be described. Thus, in this example, the ECG measurement device 10 is a transmitting device, and the pulse wave measurement device 20 is a receiving device. Note that the "send" may also be used instead of "transmit". The biometric data measurement system 1 is a system that calculates PTT without sharing information indicative of the time exemplified below between the ECG measurement device 10 and the pulse wave measurement device 20. The ECG measurement device 10 sets a first reference time corresponding to an occurrence time of a first feature value of the ECG, as described below, on the basis of the measurement of the ECG, but does not transmit information indicative of the first reference time to the pulse wave measurement device 20. As such, the ECG measurement device 10 and the pulse wave measurement device 20 do not share information indicative of the first reference time. Also, the pulse wave measurement device 20 sets a second reference time corresponding to an occurrence time of a second feature value of the pulse wave, as described below, on the basis of the measurement of the pulse wave, but does not transmit information indicative of the second reference time to the ECG measurement device 10. As such, the ECG measurement device 10 and the pulse wave measurement device 20 do not share information indicative of the second reference time.

The ECG measurement device 10 is a device for measuring ECG. The ECG measurement device 10 is disposed with two electrodes 103 on either side of the heart of a human body. Note that the position where the ECG measurement device 10 is disposed may be the upper arm of the human body, but is not limited thereto. The configuration of the ECG measurement device 10 will be described below. ECG waveform data is an example of biometric data. The ECG waveform data may be simply referred to as ECG. The ECG waveform data is also referred to as first biometric data.

The pulse wave measurement device 20 is a device for measuring pulse waves. The pulse wave measurement device 20 is placed at a predetermined position on the human body. The position where the pulse wave measurement device 20 is disposed may be at or near the wrist of the human body, but is not limited thereto. The configuration of the pulse wave measurement device 20 will be described below. Pulse wave waveform data is an example of biometric data. The pulse wave waveform data may be simply referred to as pulse wave. The pulse wave waveform data is also referred to as second biometric data.

ECG Measurement Device
Hardware Configuration

Figure 3:
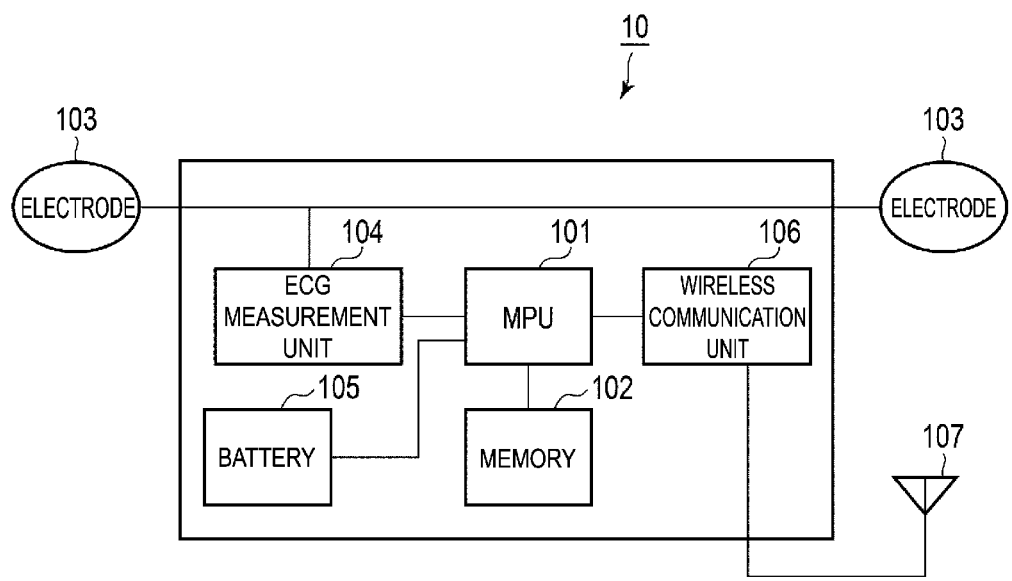
FIG. 3 is a block diagram illustrating an example of the hardware configuration of an ECG measurement device according to the present embodiment.

FIG. 3 is a block diagram illustrating an example of the hardware configuration of the ECG measurement device 10.

The ECG measurement device 10 is provided with a micro processing unit (MPU) 101, a memory 102, a plurality of electrodes 103, an ECG measurement unit 104, a battery 105, a wireless communication unit 106, and an antenna 107.

The MPU 101 executes control and various processing for each element of the ECG measurement device 10. The MPU 101 is an example of a processor. The MPU 101 deploys a program stored in the memory 102 to be described later for executing the ECG measurement device 10. The MPU 101 is capable of executing each of the units described in the software configuration section by interpreting and executing the deployed programs.

The memory 102 is an element that stores programs and various data. For example, the memory 102 is a semiconductor memory. The memory 102 stores a program executed by the MPU 101. The program is capable of executing the ECG measurement device 10 as each of the units described in the software configuration section. Note that the program may be stored in the memory 102 in advance. The program may be downloaded to the ECG measurement device 10 via a network.

The plurality of electrodes 103 are electrodes for ECG measurements. For example, the plurality of electrodes 103 includes two electrodes. The plurality of electrodes 103 are applied to a predetermined position on the human body. The plurality of electrodes 103 are preferably placed at positions on either side of the heart of the human body, but is not limited thereto and may be disposed on the upper arm of the human body, for example.

The ECG measurement unit 104 is an element for measuring ECG by measuring the potential difference generated between the plurality of electrodes 103. For example, the ECG measurement unit 104 includes an amplifier, a filter, and the like.

The battery 105 is an element that stores electrical energy and supplies power to each element of the ECG measurement device 10. For example, the battery 105 is a rechargeable battery. The power supply from the battery 105 to each element of the ECG measurement device 10 is controlled by the MPU 101.

The wireless communication unit 106 is an element that transmits a signal to the pulse wave measurement device 20 via the antenna 107. The wireless communication unit 106 is an example of a transmission unit. For example, the wireless communication unit 106 includes an interface for wireless communication. The wireless communication unit 106 transmits a signal on the basis of an instruction from the MPU 101. The wireless communication unit 106 can be in either a power being supplied state or a non-power being supplied state by control of the MPU 101. Alternatively, the wireless communication unit 106 may be in either a high power being supplied state or a low power being supplied state by control of the MPU 101. The signal includes an individual identification number. The individual identification number is information for identifying the ECG measurement device 10. The protocol for wireless communication may be any protocol, and is not limited.

Note that, with respect to a specific hardware configuration of the ECG measurement device 10, components can be omitted, replaced, or added as appropriate.

Software Configuration

FIG. 4 is a block diagram illustrating an example of the hardware configuration of the ECG measurement device 10.

The MPU 101 implements an acquisition unit 1011, a setting unit 1012, and an instruction unit 1013. Note that each of the units may be implemented by the other element constituting the ECG measurement device 10 other than the MPU 101.

The acquisition unit 1011 will now be described.

The acquisition unit 1011 acquires, in real-time, ECG waveform data from the ECG measurement unit 104. The acquisition unit 1011 outputs the ECG waveform data to the setting unit 1012.

The setting unit 1012 will now be described.

The setting unit 1012 sets the first reference time corresponding to an occurrence time of the first feature value of the ECG, as exemplified below. The first feature value is a characteristic state of the ECG. For example, the first feature value is, but is not limited to, the peak or a rise in the ECG. For example, the occurrence time is, but is not limited to, an occurrence time of the peak or an occurrence time of a rise in the ECG. The setting unit 1012 observes changes over time in the ECG, and detects the first feature value after the fact. The setting unit 1012 detects an occurrence time of the first feature value on the basis of the detection of the first feature value. The setting unit 1012 sets the first reference time corresponding to the occurrence time of the first feature value on the basis of the detection of the occurrence time of the first feature value. The setting unit 1012 outputs a setting result including information indicative of the setting of the first reference time and information indicative of the first reference time to the instruction unit 1013.

The instruction unit 1013 will now be described.

The instruction unit 1013 outputs, to the wireless communication unit 106, an instruction for causing a signal to be transmitted from the wireless communication unit 106 at a time when the predetermined first time period has elapsed since the first reference time, on the basis of the setting result from the setting unit 1012. In this way, the wireless communication unit 106 can transmit a signal at a time when the predetermined first time period has elapsed since the first reference time.

Here, the first time period will be described. The first time period is a delay time from the first reference time until the signal is transmitted. The reason of transmitting of the signal being delayed from the first time period by the first reference time is because the setting unit 1012 can only detect the first feature value after the fact. The first time period can also be referred to as a period for detecting the first feature value. The first time period is a fixed time period. The length of the first time period may be within one beat in the ECG or greater than one beat. Note that when the length of the first time period is equal to or greater than one beat, the period for detecting the first feature value will be long. As such, the setting unit 1012 can accurately detect the first feature value.

The instruction unit 1013 may control switching the wireless communication unit 106 from a non-transmittable state to a transmittable state just before the time when the wireless communication unit 106 transmits a signal. The instruction unit 1013 may control switching the wireless communication unit 106 from a transmittable state to a non-transmittable state just after the time when the wireless communication unit 106 transmits a signal. The non-transmittable state is a state in which signals cannot be transmitted from the wireless communication unit 106. The transmittable state is a state in which signals can be transmitted from the wireless communication unit 106. For example, the non-transmittable state is a state in which power is not supplied to the wireless communication unit 106, and the transmittable state is a state in which power is supplied to the wireless communication unit 106. Alternatively, the non-transmittable state may be a state in which low power is supplied to the wireless communication unit 106, and the transmittable state may be a state in which high power is supplied to the wireless communication unit 106. The wireless communication unit 106 can transmit a signal in the transmittable state. On the other hand, because the wireless communication unit 106 does not need to transmit a signal in the non-transmittable state, power is not supplied or low power is supplied. This allows the ECG measurement device 10 to reduce power consumption during periods other than when signals are transmitted.

Pulse Wave Measurement Device
Hardware Configuration

FIG. 5 is a block diagram illustrating an example of the hardware configuration of the pulse wave measurement device 20.

The pulse wave measurement device 20 is a device that receives a signal transmitted by the ECG measurement device 10 at a time when the first time period has elapsed since the first reference time, which corresponds to the first feature value of the ECG. Also, the pulse wave measurement device 20 is a device for calculating PTT on the basis of reception of a signal from the ECG measurement device 10 and estimates blood pressure on the basis of the PTT.

The pulse wave measurement device 20 includes a MPU 201, a memory 202, a battery 203, a pulse wave sensor 204, an antenna 205, a wireless communication unit 206, a cuff 207, a pump 208, a blood pressure monitor control unit 209, and a display unit 210.

The MPU 201 executes control and various processing for each element of the pulse wave measurement device 20. The MPU 201 is an example of a processor. The MPU 201 deploys a program stored in the memory 202 to be described later for executing the pulse wave measurement device 20. The MPU 201 is capable of executing the units described in the software configuration section by interpreting and executing the deployed programs.

The memory 202 is an element that stores programs and various data. For example, the memory 202 is a semiconductor memory. The memory 202 stores a program executed by the MPU 201. The program is capable of executing the pulse wave measurement device 20 as each of the units described in the software configuration section. Note that the program may be stored in the memory 202 in advance. The program may be downloaded to the pulse wave measurement device 20 via a network.

The battery 203 is an element that stores electrical energy and supplies power to each element of the pulse wave measurement device 20. For example, the battery 203 is a rechargeable battery. The power supply from the battery 203 to each element of the pulse wave measurement device 20 is controlled by the MPU 201.

The pulse wave sensor 204 is a sensor for measuring pulse waves. The pulse wave sensor 204 is placed at a predetermined position on the human body. The position where the pulse wave sensor 204 is disposed may be at or near the wrist of the human body, but is not limited thereto. The pulse wave sensor 204 is an example of a measurement unit.

The antenna 205 receives a signal from the ECG measurement device 10 and passes the signal to the wireless communication unit 206.

The wireless communication unit 206 is an element that receives a signal from the ECG measurement device 10 via the antenna 205. The wireless communication unit 206 is an example of a reception unit. For example, the wireless communication unit 206 includes an interface for wireless communication. The wireless communication unit 206 detects a reception time of a signal on the basis of the reception of a signal from the ECG measurement device 10. The wireless communication unit 206 outputs, to the MPU 201, a reception result indicating that a signal has been received and the reception time of the signal.

The wireless communication unit 206 can be in either a power being supplied state or a non-power being supplied state by control of the MPU 201. Alternatively, the wireless communication unit 206 may be in either a high power being supplied state or a low power being supplied state by control of the MPU 201.

The cuff 207 is configured to compress a target measurement site of a human body during a blood pressure measurement.

The pump 208 supplies a fluid to the cuff 207.

The blood pressure monitor control unit 209 is a processing circuit that controls the pump 208 and executes blood pressure measurement. The blood pressure monitor control unit 209 initiates blood pressure measurement on the basis of a blood pressure measurement instruction from the MPU 201.

The display unit 210 is an element for displaying information. For example, the display unit 210 is a liquid crystal display.

Note that, with respect to a specific hardware configuration of the pulse wave measurement device 20, components can be omitted, replaced, or added as appropriate.

Software Configuration

FIG. 6 is a block diagram illustrating an example of the software configuration of the pulse wave measurement device 20.

The MPU 201 implements an acquisition unit 2011, a setting unit 2012, a switching unit 2013, a determination unit 2014, a calculation unit 2015, an adjustment unit 2016, and a measurement processing unit 2017. Note that each of the units may be implemented by another element constituting the pulse wave measurement device 20 other than the MPU 201.

The acquisition unit 2011 will now be described.

The acquisition unit 2011 acquires, in real-time, pulse wave waveform data from the pulse wave sensor 204. The acquisition unit 2011 outputs the pulse wave waveform data to the setting unit 2012.

The setting unit 2012 will now be described.

The setting unit 2012 sets the second reference time corresponding to an occurrence time of the second feature value of the pulse wave, as exemplified below. The second feature value is a characteristic state of the pulse wave. For example, the second feature value is, but is not limited to, the peak or a rise in the pulse wave. Note that the second feature value is the same type of feature value as the first feature value. Thus, in the case in which the first feature value is the peak in an ECG, the second feature value is the peak in a pulse wave. In the case in which the first feature value is a rise in an ECG, the second feature value is a rise in a pulse wave. For example, the occurrence time is, but is not limited to, an occurrence time of the peak or an occurrence time of a rise in the pulse wave. Note that because the detection accuracy of a rise is higher than that of a peak, the first feature value and the second feature value are preferably a rise rather than a peak. The setting unit 2012 observes changes over time in the pulse wave, and detects the second feature value after the fact. The setting unit 2012 detects an occurrence time of the second feature value on the basis of the detection of the second feature value. The setting unit 2012 sets the second reference time corresponding to the occurrence time of the second feature value on the basis of the detection of the occurrence time of the second feature value. The setting unit 2012 outputs a setting result including information indicative of the setting of the second reference time and information indicative of the second reference time to the switching unit 2013, the determination unit 2014, and the calculation unit 2015.

The switching unit 2013 will now be described.

The switching unit 2013 controls the wireless communication unit 206, as exemplified below, on the basis of the setting result from the setting unit 2012. The switching unit 2013 references information indicative of the second reference time included in the setting result from the setting unit 2012. The switching unit 2013 switches the wireless communication unit 206 from a non-receivable state to a reception awaiting state at a time when the second time period has elapsed since the second reference time. The non-receivable state is a state in which signal reception is stopped. The reception awaiting state is a state in which the signal is awaited. The switching unit 2013 maintains the wireless communication unit 206 in the reception awaiting state during a third time period from a time when the second time period has elapsed since the second reference time. At a time after the third time period has elapsed, the switching unit 2013 switches the wireless communication unit 206 from the reception awaiting state to the non-receivable state.

The second time period and the third time period will now be described. The second time period is a time period for setting the starting time of the third time period. The third time period is a time period for awaiting a signal. The length of the third time period is set to have a length that is equal to or greater than a predetermined time period with ample time. The reason for this is that, depending on a change in the PTT due to fluctuations in the blood pressure, the period from the second reference time to the reception time of a signal by the pulse wave measurement device 20 changes. Note that the second time period and the third time period are time periods that may be changed. The length of the second time period and the third time period are adjusted as appropriate by the adjustment unit 2016, described below, so that the signal from the ECG measurement device 10 arrives within the third time period. Information indicative of the length of the second time period and information indicative of the length of the third time period are stored in the memory 202.

The non-receivable state and the reception awaiting state will now be described. For example, the non-receivable state is a state in which power is not supplied to the wireless communication unit 206, and the reception awaiting state is a state in which power is supplied to the wireless communication unit 206. Alternatively, the non-receivable state may be a state in which low power is supplied to the wireless communication unit 206, and the reception awaiting state may be a state in which high power is supplied to the wireless communication unit 206. Since the signal from the ECG measurement device 10 is likely to arrive within the third time period, the wireless communication unit 206 needs to be activated. As such, the wireless communication unit 206 is in the reception awaiting state in the third time period. The wireless communication unit 206 can receive a signal during the third time period. On the other hand, a signal from the ECG measurement device 10 is unlikely to arrive in time periods other than the third time period. The wireless communication unit 206 need not wait for a signal from the ECG measurement device 10 during time periods other than the third time period. As such, the wireless communication unit 206 is in the non-receivable state in time periods other than the third time period. The wireless communication unit 206 is supplied with no power or low power in periods other than the third time period. This allows the pulse wave measurement device 20 to reduce power consumption during periods other than the third time period.

The determination unit 2014 will be described.

As exemplified below, the determination unit 2014 determines whether or not a signal is received by the wireless communication unit 206 within the third time period. The determination unit 2014 acquires information indicative of the setting result from the setting unit 2012, and information indicative of the second time period and information indicative of the third time period from the memory 202. The determination unit 2014 references these pieces of information and counts the third time period. The determination unit 2014 acquires the reception result from the wireless communication unit 206. The determination unit 2014 may determines whether or not a signal is received by the wireless communication unit 206 within the third time period, according to whether or not the reception result has been acquired from the wireless communication unit 206 during the count of the third time period. In the case in which the reception result has been acquired from the wireless communication unit 206 during the count of the third time period, the determination unit 2014 determines that a signal has been received by the wireless communication unit 206 within the third time period. On the other hand, in the case in which the reception result has not been acquired from the wireless communication unit 206 during the count of the third time period, the determination unit 2014 determines that a signal has not been received by the wireless communication unit 206 within the third time period.

Furthermore, as exemplified below, the determination unit 2014 determines whether or not the reception time of the signal is a predetermined time within the third time period. The determination unit 2014 counts from the starting time of the third time period to the end time of the third time period. The determination unit 2014 compares the third time period and the reception time of the signal included in the reception result from the wireless communication unit 206. In this way, the determination unit 2014 determines whether or not the reception time of the signal is a predetermined time within the third time period. For example, the predetermined time is, but is not limited to, a center point in time of the third time period. The predetermined time may be any time included in a predetermined range including a center point in time of the third time period.

The determination unit 2014 outputs the determination result to the adjustment unit 2016. The determination result includes information indicative of whether or not a signal has been received by the wireless communication unit 206 within the third time period. The determination result includes information indicative of whether or not the reception time of the signal is a predetermined time within the third time period.

The calculation unit 2015 will be described.

The calculating unit 2015 executes the processing exemplified below.

The calculation unit 2015 calculates the fourth time period from the second reference time to the reception time of the signal. Here, the calculation unit 2015 references information indicative of the reception time of the signal included in the reception result from the wireless communication unit 206 and information indicative of the second reference time included in the setting result from the setting unit 2012. The calculation unit 2015 outputs information indicative of the length of the fourth time period to the adjustment unit 2016.

Furthermore, the calculation unit 2015 calculates the PTT on the basis of the time difference between the first time period and the fourth time period. PTT is based on the interval between the first reference time and the second reference time, however the difference in time between the first time period and the fourth time period corresponds to the interval between the first reference time and the second reference time. Note that the information indicative of the length of the first time period may be stored in the memory 202 in advance. Alternatively, information indicative of the length of the first time period may be included in the signal from the wireless communication unit 206. In this way, the calculation unit 2015 can calculate the PTT on the basis of the predetermined first time period and the fourth time period measured by the pulse wave measurement device 20 without sharing information indicative of the first reference time between the ECG measurement device 10 and the pulse wave measurement device 20.

The calculation unit 2015 estimates blood pressure on the basis of PTT. In the case in which the estimated blood pressure based on the PTT varies by just a prescribed value within a predetermined time period, the calculation unit 2015 outputs a blood pressure measurement instruction to the measurement processing unit 2017.

The adjustment unit 2016 will now be described.

The adjustment unit 2016 adjusts at least one of the length of the second time period and the length of the third time period. The adjustment unit 2016 references information indicative of the length of the second time period and information indicative of the length of the third time period from the memory 202, the determination result from the determination unit 2014, and information indicative of the length of the fourth time period from the calculation unit 2015. A typical example of the adjustment processing by the adjustment unit 2016 will be described below.

The measurement processing unit 2017 will now be described.

The measurement processing unit 2017 receives a blood pressure measurement instruction from the calculation unit 2015 and outputs the blood pressure measurement instruction to the blood pressure monitor control unit 209. The measurement processing unit 2017 may display an alert on the display unit 210 on the basis of the blood pressure measurement instruction from the calculation unit 2015. It is sufficient that the alert only informs the user that the pulse wave measurement device 20 will start blood pressure measurement. The measurement processing unit 2017 may output an alert using a speaker or vibration member (not illustrated) on the basis of the blood pressure measurement instruction from the calculation unit 2015. The measurement processing unit 2017 may output an alert screen data on various devices such as a smartphone (not illustrated) via the wireless communication unit 206 on the basis of the blood pressure measurement instruction from the calculation unit 2015.

Transmission and Reception Timing

The timing of the transmission and the reception of a signal in the biometric data measurement system 1 will now be described.

FIG. 7 is a diagram illustrating an example of the timing of the transmission and the reception of a signal in the biometric data measurement system 1. The upper section illustrates ECG data measured by the ECG measurement device 10. The lower section illustrates pulse wave waveform data measured by the pulse wave measurement device 20. Here, the first feature value is a R-wave peak and the second feature value is the peak of the pulse wave. The timing of the transmission and reception of a signal in the ECG measurement device 10 and the pulse wave measurement device 20 is set to match or substantially match the cycle of the pulse wave.

A first reference time $t_{1-1}$ corresponds to the occurrence time of the R-wave peak. The ECG measurement device 10 transmits a signal at a time $t_{4-1}$ when a first time period $T_{1-1}$ has elapsed since the first reference time $t_{1-1}$. The wireless communication unit 106 may switch from the non-transmittable state to the transmittable state just before the time $t_{4-1}$ by control of the MPU 101. The wireless communication unit 106 may switch from the transmittable state to the non-transmittable state just after the time $t_{4-1}$ by control of the MPU 101. A second reference time $t_{2-1}$ corresponds to the occurrence time of the peak of the pulse wave. The wireless communication unit 206 switches from the non-receivable state to the reception awaiting state at a time $t_{3-1}$ when a second time period $T_{2-1}$ has elapsed since the second reference time $t_{2-1}$ by control of the MPU 101. The wireless communication unit 206 is maintained in the reception awaiting state during a third time period $T_{3-1}$ from the time $t_{3-1}$ when a second time period $T_{2-1}$ has elapsed since the second reference time $t_{2-1}$ by control of the MPU 101. The wireless communication unit 206 receives a signal at the time $t_{4-1}$. The wireless communication unit 206 switches from the reception awaiting state to the non-receivable state at a time $t_{5-1}$ after the third time period $T_{3-1}$ has elapsed, by control of the MPU 201. A fourth time period $T_{4-1}$ is a time period from the second reference time $t_{2-1}$ to the time $t_{4-1}$, which is the reception time of the signal. The difference in time between the first time period $T_{1-1}$ and the fourth time period $T_{4-1}$ corresponds to the PTT, i.e., the interval between the first reference time $t_{1-1}$ and the second reference time $t_{2-1}$.

3. OPERATION EXAMPLE

ECG Measurement Device
Transmission Processing

Signal transmission processing by the ECG measurement device 10 will now be described.

FIG. 8 is a flowchart illustrating an example of signal transmission processing by the ECG measurement device 10. Note that the processing procedure described below is merely an example, and each process may be changed to the extent possible. Further, in the processing procedure described below, steps can be omitted, substituted, and added as appropriate.

The ECG measurement unit 104 measures the ECG (STEP101). In STEP101, the ECG measurement unit 104 measures the ECG as described above.

The setting unit 1012 sets the first reference time (STEP102). In STEP102, the setting unit 1012 sets the first reference time corresponding to an occurrence time of the first feature value of the ECG.

The wireless communication unit 106 transmits a signal at a time when the predetermined first time period has elapsed since the first reference time (STEP103). In STEP103, the wireless communication unit 106 transmits a signal on the basis of an instruction from the instruction unit 1013.

In this way, the ECG measurement device 10 repeatedly transmits, every time the first feature value is detected, a signal at a time when the first time period has elapsed since the first reference time. On the other hand, the ECG measurement device 10 disables signal transmission when the first feature value cannot be detected. By disabling signal transmission on the basis of an unreliable detection of the first feature value, the ECG measurement device 10 can prevent a decrease in the measurement accuracy of PTT in the pulse wave measurement device 20. Furthermore, since the wireless communication unit 106 does not unnecessarily transmit signals to the pulse wave measurement device 20, the ECG measurement device 10 can reduce power consumption.

Note that in STEP102, the setting unit 1012 may compare the first feature value to a preset criterion. The criterion is based on the detection reliability of the first feature value. The criterion can be discretionarily set according to the desired detection reliability of the first feature value. The indicator constituting the criterion is not particularly limited. When the first feature value satisfies the criterion, the setting unit 1012 sets the first reference time corresponding to the occurrence time of the first feature value. On the other hand, when the first feature value does not satisfy the criterion, the setting unit 1012 does not set the first reference time corresponding to the occurrence time of the first feature value. Thus, when the first feature value does not meet the criterion, the ECG measurement device 10 can disable signal transmission. By disabling signal transmission on the basis of detection of the first feature value not satisfying the criterion, the ECG measurement device 10 can prevent a decrease in the measurement accuracy of PTT in the pulse wave measurement device 20. Furthermore, since the wireless communication unit 106 does not unnecessarily transmit signals to the pulse wave measurement device 20, the ECG measurement device 10 can reduce power consumption.

Pulse Wave Measurement Device
Reception Processing

The signal reception processing by the pulse wave measurement device 20 will now be described.

FIG. 9 is a flowchart illustrating an example of signal reception processing by the pulse wave measurement device 20. Note that the processing procedure described below is merely an example, and each process may be changed to the extent possible. Further, in the processing procedure described below, steps can be omitted, substituted, and added as appropriate.

The pulse wave sensor 204 measures a pulse wave (STEP201). The setting unit 2012 sets the second reference time (STEP202). In STEP202, the setting unit 2012 sets the second reference time corresponding to an occurrence time of the second feature value of the pulse wave. When the setting unit 2012 sets the second reference time (Yes in STEP202), the switching unit 2013 controls the wireless communication unit 206 (STEP203). In STEP203, the switching unit 2013 maintains the wireless communication unit 206 in the reception awaiting state during the third time period from a time when the second time period has elapsed since the second reference time. In this way, the wireless communication unit 206 maintains the reception awaiting state and awaits a signal during the third time period from a time when the second time period has elapsed since the second reference time. When the setting unit 2012 does not set the second reference time (No in STEP202), the setting unit 2012 repeats the processing of STEP202 until the second reference time is set. Until the setting unit 2012 sets the second reference time, the wireless communication unit 206 maintains the non-receivable state.

At a time after the third time period has elapsed, the switching unit 2013 switches the wireless communication unit 206 from the reception awaiting state to the non-receivable state (STEP204). In this way, the wireless communication unit 206 switches from the reception awaiting state to the non-receivable state at a time after the third time period has elapsed.

The determination unit 2014 determines whether or not a signal is received by the wireless communication unit 206 within the third time period (STEP205). When the determination unit 2014 determines that a signal has been received within the third time period (Yes in STEP205), the calculation unit 2015 calculates the PTT (STEP206). In STEP206, the calculation unit 2015 calculates the PTT on the basis of the time difference between the first time period and the fourth time period. When the determination unit 2014 determines that a signal has not been received within the third time period (No in STEP205), the determination unit 2014 determines whether or not a non-reception of a signal within the third time period has successively occurred a predetermined number of times (STEP207). Note that the predetermined number of times can be discretionarily set.

When the non-reception of a signal within the third time period has not successively occurred a predetermined number of times (No in STEP207), the setting unit 2012 executes the processing of STEP202. When the non-reception of a signal within the third time period has successively occurred a predetermined number of times (Yes in STEP207), the adjustment unit 2016 adjusts at least one of the length of the second time period and the length of the third time period (STEP208). In STEP208, the adjustment unit 2016 adjusts at least one of the length of the second time period and the length of the third time period on the basis of the non-reception of a signal successively occurring a predetermined number of times within the third time period. The adjustment unit 2016 updates the information indicative of the length of the second time period stored in the memory 202 on the basis of the adjustment of the length of the second time period. In a similar manner, the adjustment unit 2016 updates the information indicative of the length of the third time period stored in the memory 202 on the basis of the adjustment of the length of the third time period.

As described in STEP202, until the setting unit 2012 sets the second reference time, the wireless communication unit 206 maintains the non-receivable state. In other words, when the setting unit 2012 has not set the second reference time, the wireless communication unit 206 does not switch from the non-receivable state to the reception awaiting state. The pulse wave measurement device 20 can disable switching from the non-receivable state to the reception awaiting state on the basis of an unreliable detection of the second feature value. This allows the pulse wave measurement device 20 to avoid receiving signals from the ECG measurement device 10 and prevent a decrease in the measurement accuracy of the PTT. Furthermore, because the wireless communication unit 206 does not undesirably switch from the non-receivable state to the reception awaiting state, the pulse wave measurement device 20 can reduce power consumption.

Note that in STEP202, the setting unit 2012 may compare the second feature value to a preset criterion. The criterion is based on the detection reliability of the second feature value. The criterion can be discretionarily set according to the desired detection reliability of the second feature value. The indicator constituting the criterion is not particularly limited. When the second feature value satisfies the criterion, the setting unit 2012 sets the second reference time corresponding to the occurrence time of the second feature value. On the other hand, when the second feature value does not satisfy the criterion, the setting unit 2012 does not set the second reference time corresponding to the occurrence time of the second feature value. In this way, when the second feature value does not satisfy the criterion, the wireless communication unit 206 does not switch from the non-receivable state to the reception awaiting state. The pulse wave measurement device 20 can avoid receiving signals from the ECG measurement device 10 and prevent a decrease in the measurement accuracy of the PTT. Furthermore, because the wireless communication unit 206 does not undesirably switch from the non-receivable state to the reception awaiting state, the pulse wave measurement device 20 can reduce power consumption.

Note that in STEP207, the adjustment unit 2016 may adjust at least one of the length of the second time period and the length of the third time period as described below. The adjustment unit 2016 may change the length of the third time period while the length of the second time period remains unchanged. The adjustment unit 2016 may change the length of the second time period while the length of the third time period remains unchanged. The adjustment unit 2016 may change both of the length of the second time period and the length of the third time period. Note that the adjustment unit 2016 preferably at least adjusts the length of the third time period to be longer. While this lengthens the third time period, the wireless communication unit 206 can reliably receive a signal even when the change in PTT is greater than assumed.

Adjustment Processing

An example of adjustment processing by the pulse wave measurement device 20 will now be described.

FIG. 10 is a flow chart illustrating an example of adjustment processing by the pulse wave measurement device 20. By the adjustment processing exemplified in FIG. 10, the pulse wave measurement device 20 sets, every time signal is received, an optimal second time period. Note that the processing procedure described below is merely an example, and each process may be changed to the extent possible. Further, in the processing procedure described below, steps can be omitted, substituted, and added as appropriate.

The wireless communication unit 206 receives a signal from the ECG measurement device 10 (STEP301). The adjustment unit 2016 determines whether or not the reception time of the signal is a predetermined time within the third time period (STEP302). In STEP302, the adjustment unit 2016 references information, included in the determination result from the determination unit 2014, indicative of whether or not the reception time of the signal is a predetermined time within the third time period. When the reception time of the signal is a predetermined time within the third time period (Yes in STEP302), the pulse wave measurement device 20 ends the adjustment processing.

When the reception time of the signal is not a predetermined time within the third time period (No in STEP302), the adjustment unit 2016 adjusts the length of the second time period (STEP303). In STEP303, the adjustment unit 2016 adjusts the length of the second time period so that the reception time of the signal is brought closer to a predetermined time (for example, a center point in time) within the third time period. The adjustment unit 2016 can refer to the length of the most recent fourth time period. The adjustment unit 2016 may refer to the average length of a plurality of previous fourth time periods. The adjustment unit 2016 can adjust the length of the second period so that the end time of the fourth time period corresponding to the reception time of the signal matches or substantially matches a predetermined time within the third time period. The adjustment unit 2016 updates the information indicative of the length of the second time period stored in the memory 202 on the basis of the adjustment of the length of the second time period.

Another example of adjustment processing will now be described.

FIG. 11 is a flow chart illustrating another example of adjustment processing by the pulse wave measurement device 20. The pulse wave measurement device 20 learns a fourth time period for each user by the adjustment processing exemplified in FIG. 11 and sets an optimal second time period and third time period for each user. For example, the pulse wave measurement device 20 executes the adjustment processing exemplified in FIG. 11 at the time of initial setup or reset. Note that the processing procedure described below is merely an example, and each process may be changed to the extent possible. Further, in the processing procedure described below, steps can be omitted, substituted, and added as appropriate.

The wireless communication unit 206 receives a signal from the ECG measurement device 10 (STEP401). The calculation unit 2015 calculates the fourth time period (STEP402). In STEP402, the calculation unit 2015 calculates the fourth time period on the basis of information indicative of the second reference time and information indicative of the reception time of the signal.

The adjustment unit 2016 adjusts at least one of the length of the second time period and the length of the third time period (STEP403). In STEP403, for example, in a similar manner to STEP303, the adjustment unit 2016 adjusts the length of the second time period so that the end time of the fourth time period corresponding to the reception time of the signal is brought closer to a predetermined time within the third time period. The adjustment unit 2016 updates the information indicative of the length of the second time period stored in the memory 202 on the basis of the adjustment of the length of the second time period. In STEP403, for example, the adjustment unit 2016 adjusts the length of the third time period to shorten the length of the third time period. The adjustment unit 2016 may shorten the length of the third time period by a predetermined proportion or may shorten the length of the third time period by a predetermined length. The adjustment unit 2016 updates the information indicative of the length of the third time period stored in the memory 202 on the basis of the adjustment of the length of the third time period.

The adjustment unit 2016 determines whether or not the length of the third time period is equal to the length of a predetermined time period (STEP404). In STEP404, the adjustment unit 2016 determines whether or not the third time period has been shortened to be equal to the length of the predetermined time period. When the length of the third time period is equal to the length of the predetermined time period (Yes in STEP404), the pulse wave measurement device 20 ends the adjustment processing. When the length of the third time period is not equal to the length of the predetermined time period (No in STEP404), the pulse wave measurement device 20 repeats the processing from STEP401 to STEP404. A case in which length of the third time period being not equal to the length of the predetermined period corresponds to a case in which the length of the third time period is longer than the length of the predetermined time period.

In this way, the adjustment unit 2016 adjusts at least one of the length of the second time period and the length of the third time period for each calculation of the fourth time period. For example, the adjustment unit 2016 adjusts the length of the second time period for each calculation of the fourth time period and adjusts the start time and the end time of the third time period. For example, the adjustment unit 2016 incrementally shortens the length of the third time period for each calculation of the fourth period until the length of the third time period is equal to the length of the predetermined period. For example, at the time of initial setup or reset, the wireless communication unit 206 may maintain the reception awaiting state for all time periods, and the adjustment unit 2016 may incrementally shorten, for each calculation of the fourth time period, the length of the third time period corresponding to the reception awaiting state.

4 ACTION AND EFFECT

As described above, in the present embodiment, the biometric data measurement system 1 includes the ECG measurement device 10 provided with the wireless communication unit 106 that transmits a signal at a time when the first time period has elapsed since the first reference time and the pulse wave measurement device 20 provided with the wireless communication unit 206 that maintains the reception awaiting state during the third time period from a time when the second time period has elapsed since the second reference time.

In this way, the timing of the signal transmission by the ECG measurement device 10 is determined on the basis of the first reference time, which corresponds to the occurrence time of the first feature value in the ECG. The ECG measurement device 10 is at least only required to transmit a signal at the time when the first time period has elapsed since the first reference time. The ECG measurement device 10 is not necessarily required to constantly ensure a communicative state. As such, the ECG measurement device 10 can reduce the power consumption required for communication.

Furthermore, the third time period for awaiting a signal is determined on the basis of the second reference time corresponding to the occurrence time of the second feature value in the pulse wave. The pulse wave measurement device 20 can successfully communicate with the ECG measurement device 10 as long as the pulse wave measurement device 20 is awaiting the signal in the third time period. The pulse wave measurement device 20 is not necessarily required to constantly ensure a communicative state. As such, the pulse wave measurement device 20 can reduce the power consumption required for communication.

Accordingly, the biometric data measurement system 1 can not only be easily attached to the human body, but also can reduce power consumption.

Furthermore, the ECG measurement device 10 and the pulse wave measurement device 20 can communicate wirelessly without a decrease in measurement accuracy of the biometric data. As such, the user can easily attach the ECG measurement device 10 and the pulse wave measurement device 20.

Furthermore, the ECG measurement device 10 and the pulse wave measurement device 20 communicate with passive operations. As such, the ECG measurement device 10 and the pulse wave measurement device 20 can reduce power consumption, making it possible to reduce the time and effort to charge. In addition, the battery size of the ECG measurement device 10 and the pulse wave measurement device 20 is reduced, so the battery cost is reduced. As the battery size is made smaller, the size of the ECG measurement device 10 and the pulse wave measurement device 20 itself is reduced.

In addition, the device cost is reduced because the ECG measurement device 10 and the pulse wave measurement device 20 may be configured to communicate in an existing method.

In the present embodiment, the pulse wave measurement device 20 calculates the PTT on the basis of the time difference between the first time period and the fourth time period.

Because the timing of the ECG measurement device 10 transmitting a signal is based on the first reference time, the pulse wave measurement device 20 can calculate the PTT by simply calculating the time difference between the first time period and the fourth time period. By the pulse wave measurement device 20 being able to calculate the PTT without constantly communicating with the ECG measurement device 10, the power consumption required for communication can be reduced.

In the present embodiment, the pulse wave measurement device 20 adjusts at least one of the length of the second time period and the length of the third time period on the basis of the non-reception of a signal successively occurring a predetermined number of times within the third time period.

Depending on a change in the PTT due to fluctuations in the blood pressure, the period from the second reference time to a time when a signal arrives at the pulse wave measurement device 20 changes. The pulse wave measurement device 20 can stop continuing the state of being not able to receive a signal arriving to the pulse wave measurement device 20.

In the present embodiment, when the reception time of the signal is not at the predetermined time within the third time period, the pulse wave measurement device 20 adjusts the length of the second time period so that the reception time of the signal is brought closer to the predetermined time within the third time period.

Depending on a change in the PTT due to fluctuations in the blood pressure, the period from the second reference time to a time when a signal arrives at the pulse wave measurement device 20 may shorten or lengthen. By adjusting the length of the second time period, the pulse wave measurement device 20 can reduce the possibility of a signal not being received even when the time period from the second reference time to a time when the signal arrives at the pulse wave measurement device 20 changes depending on a change in the PTT.

In the present embodiment, the pulse wave measurement device 20 adjusts at least one of the length of the second time period and the length of the third time period for each calculation of the fourth time period.

This allows the pulse wave measurement device 20 to set an optimal second time period and third time period for each user. Furthermore, because the third time period can be shortened to the minimum necessary length, the pulse wave measurement device 20 can reduce the power consumption.

In the present embodiment, the transmitting device is the ECG measurement device 10 that measures ECG, and the receiving device is the pulse wave measurement device 20 that measures pulse waves.

The amount of power is determined by the product of power and time. The current value is larger for the ECG measurement device 10 that transmits the signal than the pulse wave measurement device 20 that receives the signal. On the other hand, the third time period during which the pulse wave measurement device 20 awaits the signal is longer than the time period in which the ECG measurement device 10 transmits the signal. As such, the amount of power consumed is larger for the pulse wave measurement device 20 than the ECG measurement device 10. Here, the quality of the pulse wave waveform may be worse than the quality of the ECG waveform. Unless the second feature value of the pulse wave is detected, the pulse wave measurement device 20 does not switch from the non-receivable state to the reception awaiting state. As such, the pulse wave measurement device 20 can reduce power consumption because it does not undesirably switch from the non-receivable state to the reception awaiting state.

5 MODIFIED EXAMPLES

5-1 Modified Example 1

In the present embodiment described above, an example in which the ECG measurement device 10 transmits a signal to the pulse wave measurement device 20 has been described, but the present invention is not limited thereto. The pulse wave measurement device 20 may be a transmitting device that transmits a signal, and the ECG measurement device 10 may be a receiving device that receives a signal. Note that the biometric data measurement system 1 that measures PTT may include two pulse wave measurement devices instead of the ECG measurement device 10 and a single pulse wave measurement device. In this case, one pulse wave measurement device is a transmitting device that transmits a signal, and the other pulse wave measurement device is a receiving device that receives a signal.

5-2 Modified Example 2

The signal transmitted from the ECG measurement device 10 to the pulse wave measurement device 20 may be transmitted using a method such as an advertisement signal or a beacon signal of Bluetooth (trade name) Low Energy (BLE) or the like. It is sufficient that the pulse wave measurement device 20 can recognize that the ECG measurement device 10 has transmitted a signal at a time when the first time period has elapsed since the first reference time on the basis of receiving the signal. Thus, the method and protocol of the signal for wireless communication is not particularly limited. The biometric data measurement system 1 can also be configured to communicate using an existing method, allowing for reduced development time.

5-3 Modified Example 3

In short, the invention is not limited to the present embodiment and can be embodied by modifying the components in an implementation stage in a range without departing from the gist thereof. Further, various inventions can be formed by appropriately combining a plurality of constituent elements disclosed in the present embodiment. For example, some constituent elements may be omitted from the entire constituent elements shown in the embodiment. Furthermore, the constituent elements of different embodiments may be combined appropriately.

6 SUPPLEMENTARY NOTES

A part or all of the present embodiment may also be described as supplementary notes below in addition to claims, which is not limited thereto.

Supplementary Note 1

A biometric data measurement system (1), including,
a transmitting device (10) including
 a measurement unit (104) configured to measure a first biometric data,
 a setting unit (1012) configured to set a first reference time corresponding to an occurrence time of a first feature value of the first biometric data, and
 a transmission unit (106) configured to transmit a signal at a time when a predetermined first time period has elapsed since the first reference time, and
a receiving device (20) including
 a measurement unit (204) configured to measure a second biometric data,
 a setting unit (2012) configured to set a second reference time corresponding to an occurrence time of a second feature value of the second biometric data, and
 a reception unit (206) configured to maintain an awaiting state for the signal in a third time period from a time when a second time period has elapsed since the second reference time.

REFERENCE SIGNS LIST

1 Biometric data measurement system
10 ECG measurement device
20 Pulse wave measurement device
101 MPU
102 Memory
103 Plurality of electrodes
104 ECG measurement unit
105 Battery
106 Wireless communication unit
107 Antenna
201 MPU
202 Memory
203 Battery
204 Pulse wave sensor
205 Antenna
206 Wireless communication unit
207 Cuff
208 Pump
209 Blood pressure monitor control unit
210 Display unit
1011 Acquisition unit
1012 Setting unit
1013 Instruction unit
2011 Acquisition unit
2012 Setting unit
2013 Switching unit
2014 Determination unit
2015 Calculation unit
2016 Adjustment unit
2017 Measurement processing unit

The invention claimed is:
1. A biometric data measurement system, comprising:
a transmitting device including:
 measurement circuitry configured to measure a first biometric data;

a first processor configured to set a first reference time corresponding to an occurrence time of a first feature value of the first biometric data; and a transmitter configured to transmit a signal at a time when a predetermined first time period has elapsed since the first reference time, the predetermined first time period being a fixed period of time for detecting the first feature value, wherein the first processor is further configured to switch the transmitter to a transmittable state where the transmitter receives first high power so as to be capable of transmitting the signal prior to the time when the predetermined first time period has elapsed and switch the transmitter to a non-transmittable state where the transmitter receives first low power or no power for power savings so as to be incapable of transmitting the signal after the time when the predetermined first time period has elapsed, the first high power being higher than the first low power; and a receiving device including:

a sensor configured to measure a second biometric data;

a second processor configured to set a second reference time corresponding to an occurrence time of a second feature value of the second biometric data; and a receiver configured to maintain an awaiting state for the signal during a third time period from a time when a second time period has elapsed since the second reference time, wherein the second processor is further configured to switch the receiver to the awaiting state where the receiver receives second high power so as to be capable of receiving the signal at the time when the second time period has elapsed and switch the receiver to a non-receivable state where the receiver receives second low power or no power for power savings so as to be incapable of receiving the signal at an end of the third time period, the second high power being higher than the second low power, and wherein the second processor is further configured to calculate a fourth time period from the second reference time to a reception time of the signal and calculate a pulse transit time (PTT) on the basis of a time difference between the first time period and the fourth time period.

2. The biometric data measurement system according to claim 1, wherein
the second processor is further configured to adjust at least one of a length of the second time period and a length of the third time period on the basis of non-reception of the signal successively occurring a predetermined number of times within the third time period.

3. The biometric data measurement system according to claim 1, wherein
the second processor is further configured to adjust a length of the second time period causing the reception time of the signal to be closer to a predetermined time within the third time period when the reception time of the signal is not the predetermined time within the third time period.

4. The biometric data measurement system according to claim 1, wherein
the second processor is further configured to adjust at least one of a length of the second time period and a length of the third time period for each calculation of the fourth time period.

5. The biometric data measurement system according to claim 1, wherein
the first biometric data is an ECG, and the second biometric data is a pulse wave.

6. A biometric data measurement method, comprising:

measuring a first biometric data by a transmitting device including a transmitter;

setting a first reference time corresponding to an occurrence time of a first feature value of the first biometric data by the transmitting device;

switching the transmitter to a transmittable state where the transmitter receives first high power so as to be capable of transmitting a signal prior to a time when a predetermined first time period has elapsed since the first reference time, the predetermined first time period being a fixed period of time for detecting the first feature value;

transmitting the signal at the time when the predetermined first time period has elapsed since the first reference time with the transmitter;

switching the transmitter to a non-transmittable state where the transmitter receives first low power or no power for power savings so as to be incapable of transmitting the signal after the time when the predetermined first time period has elapsed, the first high power being higher than the first low power;

measuring a second biometric data by a receiving device including a receiver;

setting a second reference time corresponding to an occurrence time of a second feature value of the second biometric data by the receiving device;

switching the receiver to an awaiting state where the receiver receives second high power so as to be capable of receiving the signal at a time when a second time period has elapsed since the second reference time;

maintaining the receiver in the awaiting state for the signal during a third time period from the time when the second time period has elapsed;

switching the receiver to a non-receivable state where the receiver receives second low power or no power for power savings so as to be incapable of receiving the signal at an end of the third time period, the second high power being higher than the second low power;

calculating a fourth time period from the second reference time to a reception time of the signal by the receiving device; and calculating a pulse transit time (PTT) on the basis of a time difference between the first time period and the fourth time period by the receiving device.

* * * * *